(12) United States Patent
Okoli et al.

(10) Patent No.: US 10,141,119 B2
(45) Date of Patent: Nov. 27, 2018

(54) DYE-SENSITIZED SOLAR CELLS INCLUDING CARBON NANOTUBE YARNS

(71) Applicant: Florida State University Research Foundation, Inc., Tallahassee, FL (US)

(72) Inventors: Okenwa I. Okoli, Tallahassee, FL (US); Jin Yan, Tallahassee, FL (US); Tarik J. Dickens, Tallahassee, FL (US); M. Jasim Uddin, Brownsville, TX (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 14/805,865

(22) Filed: Jul. 22, 2015

(65) Prior Publication Data

US 2016/0028033 A1  Jan. 28, 2016

Related U.S. Application Data

(60) Provisional application No. 62/027,608, filed on Jul. 22, 2014.

(51) Int. Cl.
*H01G 9/20* (2006.01)
*G01N 21/70* (2006.01)
*H01L 51/00* (2006.01)

(52) U.S. Cl.
CPC .......... *H01G 9/2086* (2013.01); *G01N 21/70* (2013.01); *H01G 9/2009* (2013.01);
(Continued)

(58) Field of Classification Search
CPC ... Y02E 10/542; H01L 51/444; H01L 51/426; H01L 51/0086; H01L 51/0048; G01N 21/70
See application file for complete search history.

(56) References Cited

U.S. PATENT DOCUMENTS

| | | | | |
|---|---|---|---|---|
| 4,981,590 A | * | 1/1991 | Van 'T Veen | ..... B01D 67/0048 210/490 |
| 2004/0161380 A1 | * | 8/2004 | Zimehl | ................... B82Y 30/00 423/610 |

(Continued)

OTHER PUBLICATIONS

Dictionary.com "Definition of microporous" Accessed online Aug. 1, 2016.*

(Continued)

*Primary Examiner* — Liesl C Baumann
(74) *Attorney, Agent, or Firm* — Eversheds Sutherland (US) LLP (57) ABSTRACT

A dye-sensitized solar cell is provided. The dye-sensitized solar cell includes a working electrode which includes a plurality of twisted carbon nanotube yarns. The dye-sensitized solar cell also includes a hybrid sensitizer. The hybrid sensitizer includes a nanoporous titanium oxide layer coated on the plurality of twisted carbon nanotube yarns, a microporous titanium oxide layer coated onto the nanoporous titanium oxide layer, and dye particles and quantum dots disposed in the pores of the microporous titanium oxide layer. In addition, the dye-sensitized solar cell includes a conducting electrode which includes at least one carbon nanotube yarn disposed about the hybrid sensitizer. The dye-sensitized solar cell also includes a solid state electrolyte disposed about the hybrid sensitizer.

13 Claims, 13 Drawing Sheets

(52) U.S. Cl.
CPC ......... *H01G 9/2031* (2013.01); *H01G 9/2059* (2013.01); *H01L 51/0048* (2013.01); *H01L 51/0086* (2013.01); *Y02E 10/542* (2013.01)

(56) References Cited

U.S. PATENT DOCUMENTS

| | | | | |
|---|---|---|---|---|
| 2006/0165404 | A1* | 7/2006 | Jung | H01G 9/2031 396/268 |
| 2007/0209696 | A1* | 9/2007 | Duerr | H01G 9/2031 136/252 |
| 2009/0217963 | A1* | 9/2009 | Liang | H01G 9/2081 136/243 |
| 2010/0259811 | A1* | 10/2010 | Wu | B82Y 20/00 359/275 |
| 2011/0056561 | A1* | 3/2011 | Burn | C07F 15/0046 136/263 |
| 2011/0088758 | A1* | 4/2011 | Yagi | C03C 8/16 136/252 |
| 2016/0093913 | A1* | 3/2016 | Saito | H01M 4/13 429/246 |

OTHER PUBLICATIONS

Tian et al. "Enhanced Performance of CdS/CdSe Quantum Dot Cosensitized Solar Cells via Homogeneous Distribution of Quantum Dots in TiO2 Film." J. Phys. Chem. C 2012, 116, 18655-18662. (Year: 2012).*

Jun et al. "Efficiency improvement of CdS and CdSe quantum dot-sensitized solar cells by TiO2 surface treatment." J. Renewable Sustainable Energy 6, 023107 (2014). (Year: 2014).*

Sudhagar et al. "The performance of coupled (CdS:CdSe) quantum dot-sensitized TiO2 nanofibrous solar cells." Electrochemistry Communications 11 (2009) 2220-2224. (Year: 2009).*

Kim et al. "Surface modification on TiO2nanoparticles in CdS/CdSe QuantumDot-sensitized Solar Cell." Electrochimica Acta 118 (2014) 118-123. Available online Dec. 2013. (Year: 2013).*

Kim et al. "The effect of TiO2 compact layer in ZnO nanorod based CdS/CdSe quantum-dot sensitized solar cell." Phys. Status Solidi A 211, No. 8, 1839-1843 (2014). (Year: 2014).*

Jun et al. "Quantum dot-sensitized solar cells—perspective and recent developments: A review of Cd chalcogenide quantum dots as sensitizers." Renewable and Sustainable Energy Reviews 22 (2013) 148-167. (Year: 2013).*

Mora-Sero et al. "Fast Regeneration of CdSe Quantum Dots by Ru Dye in Sensitized TiO2 Electrodes." J. Phys. Chem. C 2010, 114, 6755-6761. (Year: 2010).*

Mora-Sero et al. "Breakthroughs in the Development of Semiconductor-Sensitized Solar Cells." J. Phys. Chem. Lett. 2010, 1, 3046-3052. (Year: 2010).*

Zewdu et al. "Photo-induced charge transfer dynamics in efficient TiO2/CdS/CdSe sensitized solar cells." Energy Environ. Sci., 2011, 4, 4633. (Year: 2011).*

Niitsoo et al. "Chemical bath deposited CdS/CdSe-sensitized porous TiO2 solar cells." Journal of Photochemistry and Photobiology A: Chemistry 181 (2006) 306-313. (Year: 2006).*

Chi et al. "Surface modifications of CdS/CdSe co-sensitized TiO2 photoelectrodes for solid-state quantum-dot-sensitized solar cells." J. Mater. Chem., 2011, 21, 17534. (Year: 2011).*

Lee et al. "Highly Efficient Quantum-Dot-Sensitized Solar Cell Based on Co-Sensitization of CdS/CdSe." Adv. Funct. Mater. 2009, 19, 604-609. (Year: 2009).*

Yan et al. "3D Novel Photovoltaic Sensors for In-Situ Structural Health Monitoring (SHM) of Composite Materials Using Hybrid Quantum Dots (QDS)." SAMPE Conference Proceedings. Seattle, WA, Jun. 2-5, 2014. Society for the Advancement of Material and Process Engineering. (Year: 2014).*

Brown, Patrick et al., "Quantum Dot Solar Cells, Electrophoretic Deposition of CdSe—C60 Composite Films and Capture of Photogenerated Electrons with nC60 Cluster Shell," J. Am. Chem. Soc. 130, 8890-8891 (2008).

Fan, Xing et al., "Wire-Shaped Flexible Dye-Sensitized Solar Cells," Advanced Materials 20, 592-595 (2008).

Ito, Seigo et al., "High-efficiency (7.2%) flexible dye-sensitized solar cells with Ti-metal substrate for nanocrystalline-TiO2 photoanode," Chem. Commun. 4004-4006 (2006).

Kongkanand, Anusorn et al., "Quantum Dot Solar Cells. Tuning Photoresponse through Size and Shape Control of CdSe—TiO2 Architecture," J. Am. Chem. Soc. 130, 4007-4015 (2008).

Lee, Yuh-Lang et al., "CdS/CdSe Co-Sensitized TiO2 Photoelectrode for Efficient Hydrogen Generation in a Photoelectrochemical Cell," Chemistry of Materials 22, 922-927 (2009).

Lee, Yuh-Lang et al., "Highly Efficient CdSe-Sensitized TiO2 Photoelectrode for Quantum-Dot-Sensitized Solar Cell Applications," Chem. Mater. 2008, 20, 6903-6905 (2008).

O'Regan, Brian et al., "A Low-Cost, High-Efficiency Solar Cell Based on Dye-Sensitized Colloidal TiO2 Films," Nature, 353, 737-740 (1991).

Uddin, M. J. et al., "Self-aligned carbon nanotubes yarns (CNY) with efficient optoelectronic interface for microyarn shaped 3D photovoltaic cells," Solar Energy Materials & Solar Cells, 115, 166-171 (2013).

Yan, J. et al., "Carbon nanotubes (CNTs) enrich the solar cells," Solar Energy, 96, 239-252 (2013).

Yan, Jin et al., "Tailoring the efficiency of 3D wire-shaped photovoltaic cells (WPVCs) by functionalization of solid-liquid interfacial properties," Phys. Status Solidi A 210, 12, 2535-2541 (2013).

Yang, Chunyan et al., "Controlled growth, properties, and application of CdS branched nanorod arrays on transparent conducting oxide substrate," Solar Energy Materials & Solar Cells, 115, 100-107 (2013).

Zhang, Luhui et al., "Wire-supported CdSe nanowire array photoelectrochemical solar cells," Physical Chemistry Chemical Physics, 14, 3583-3588 (2012).

Zhang, Sen et al., "Porous, Platinum Nanoparticle-Adsorbed Carbon Nanotube Yarns for Efficient Fiber Solar Cells," ACS Nano, 6, 7191-7198 (2012).

Zou, Dechun et al., "Fiber-shaped flexible solar cells," Coordination Chemistry Reviews, 250, 1169-1178 (2010).

Yan et al., "3D Wire-Shaped Dye-Sensitized Solar Cells in Solid State Using Carbon Nanotube Yarns with Hybrid Photovoltaic Structure," Advanced Material Interfaces, 2014, 1, 1400075, pp. 1-7.

* cited by examiner

DYE-SENSITIZED SOLAR CELLS INCLUDING CARBON NANOTUBE YARNS

CROSS-REFERENCE TO RELATED APPLICATIONS

This disclosure claims priority to and the benefit of U.S. provisional patent application No. 62/027,608, filed Jul. 22, 2014, which is herein incorporated by reference in its entirety.

STATEMENT REGARDING FEDERALLY SPONSORED RESEARCH OR DEVELOPMENT

This invention was made with government support under CMMI0969413 awarded by the National Science Foundation. The government has certain rights in this invention.

FIELD OF THE DISCLOSURE

This disclosure is generally in the field of photovoltaics, and more particularly to composite structure solar cells.

BACKGROUND

Dye-sensitized solar cells are photoelectrochemical systems based on a semiconductor formation with a photosensitized anode, a conductive cathode, and an electrolyte. Conventional dye-sensitized solar cells include flat fluorine doped tin oxide substrates, which are rigid and thick. Due to the rigidity and thickness of typical dye-sensitized solar cells, incorporating such cells into engineering structures can be problematic. Accordingly, there is a need for a dye-sensitized solar cell with improved performance and mechanical properties.

SUMMARY

Some or all of the above needs and/or problems may be addressed by certain embodiments of the dye-sensitized solar cell disclosed herein. The dye-sensitized solar cell includes a working electrode comprising a plurality of twisted carbon nanotube yarns. The dye-sensitized solar cell also includes a hybrid sensitizer. The hybrid sensitizer comprises a nanoporous titanium oxide layer coated on the plurality of twisted carbon nanotube yarns, a microporous titanium oxide layer coated onto the nanoporous titanium oxide layer, and dye particles and quantum dots disposed in the pores of the microporous titanium oxide layer. In addition, the dye-sensitized solar cell includes a conducting electrode comprising at least one carbon nanotube yarn disposed about the hybrid sensitizer. Moreover, the dye-sensitized solar cell includes a solid state electrolyte disposed about the hybrid sensitizer.

Other features and aspects of the dye-sensitized solar cell will be apparent or will become apparent to one with skill in the art upon examination of the following figures and the detailed description. All other features and aspects, as well as other system, method, and assembly embodiments, are intended to be included within the description and are intended to be within the scope of the accompanying claims.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Systems and methods for a dye-sensitized solar cell are disclosed. In some instances, the dye-sensitized solar cell is a wire-shaped hybrid dye-sensitized solar cell. For example, the dye-sensitized solar cell may include carbon nanotube yarn electrodes, a solid state electrolyte, and quantum dots and dye particles incorporated into a photovoltaic sensitizer structure. The inclusion of the quantum dots and dye particles improves the photon absorption coefficient, tunable band gap, and multiple exciton generation (MEG) effects of the dye-sensitized solar cell. In particular, dye particles comprising N719 dye and quantum dots comprising cadmium sulfide (CdS) and cadmium selenide (CdSe) are incorporated into the photovoltaic sensitizer structure of the dye-sensitized solar cell to act as an extra electron receiver in a $TiO_2$ film. This is synthesized in a secondary process known as post-hydrothermal process. In this manner, the dye-sensitized solar cell is directed to the application of a nanoporous (np)-$TiO_2$/microporous (mp)-$TiO_2$/CdS/CdSe/N719 hybrid photovoltaic sensitizer structure to realize both MEG effects and multiple electron transmission paths.

In some embodiments, the dye-sensitized solar cell is in the form of a flexible wire-shaped structure. In this manner, the flexible, wire-shaped dye-sensitized solar cell may replace conventional dye-sensitized solar cells with similar functions. In some embodiments, the dye-sensitized solar cell forms part of a larger embeddable smart composite with intrinsic triboluminescent/mechanoluminescent (TL/ML) features. For example, the hybrid wire-shaped dye-sensitized solar cell may be used as a photovoltaic sensor in TL-based structural health monitoring (SHM) systems. In some instances, the dye-sensitized solar cell enables the capture, conversion, and transport of light signals for TL events for the detection of damage and in-situ SHM. In addition, the dye-sensitized solar cell may be used to harvest energy, such as solar energy, in systems.

Figure 1:
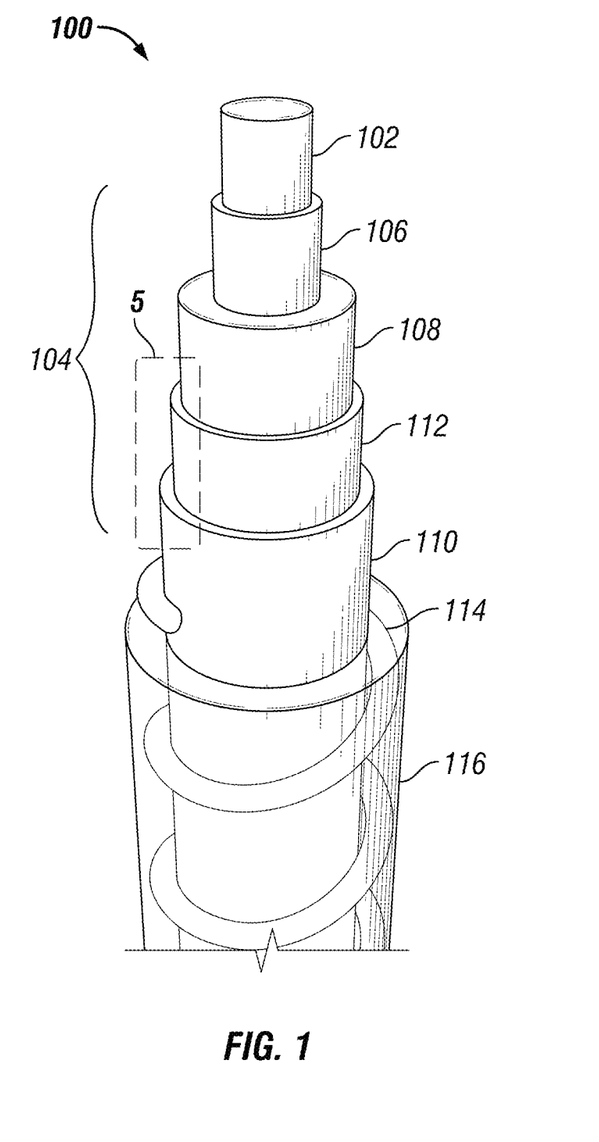
FIG. 1 schematically depicts a dye-sensitized solar cell.

FIG. 1 depicts, in a partial cut-away, perspective view, a dye-sensitized solar cell (DSSC) 100. In some instances, the DSSC 100 is used to harvest solar energy. In one embodiment, the DSSC 100 includes a flexible wire or the like. The DSSC 100 may be woven into a fabric, used as a sensor element, or used for triboluminescent/mechanoluminescent (TL/ML) structural health monitoring. For example, the DSSC 100 enables the capture, conversion, and transport of light signals for TL events for the detection of damage and in-situ system health monitoring. The DSSC 100 may be used in a variety of applications.

Figure 2:
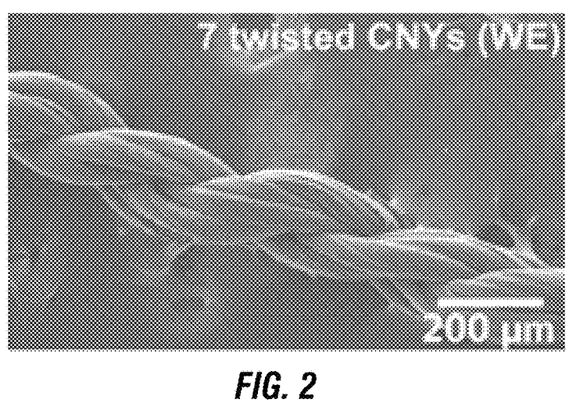
FIG. 2 depicts a scanning electron microscope (SEM) image of a working electrode comprises a plurality of twisted carbon nanotube yarns.

The DSSC 100 includes a working electrode 102. In some instances, as depicted in the scanning electron microscope image of FIG. 2, the working electrode 102 comprises a plurality of twisted carbon nanotube yarns. For example, in one embodiment, the plurality of twisted carbon nanotube yarns comprises 7 carbon nanotube yarns that are braided together. Any number of carbon nanotube yarns may be used herein. The carbon nanotube yarns may be twisted or braided in any suitable configuration.

Figure 3:
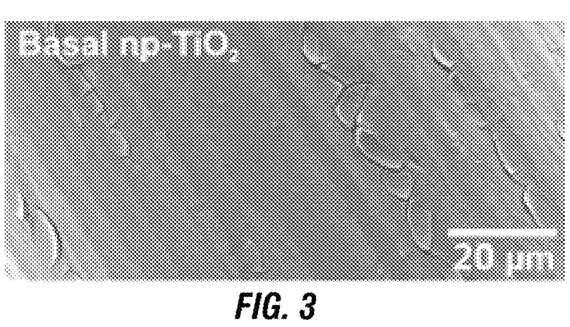
FIG. 3 depicts an SEM image of the nanoporous (np) titanium oxide layer.
Figure 4:
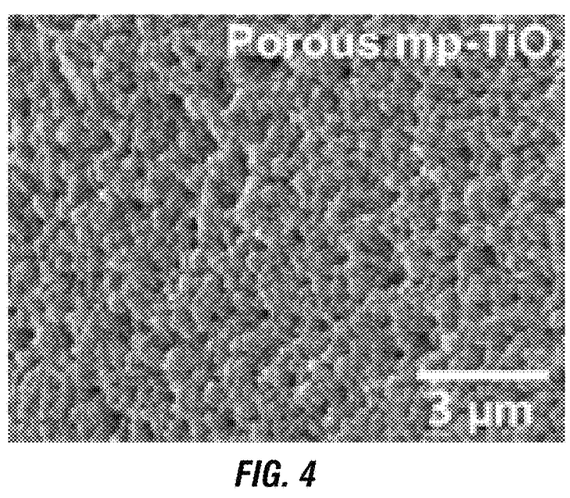
FIG. 4 depicts an SEM image the microporous (mp) titanium oxide layer.

Referring back to FIG. 1, the DSSC 100 also includes a hybrid sensitizer 104. The hybrid sensitizer 104 is a photovoltaic structure formed collectively by a nanoporous titanium oxide layer 106, a microporous titanium oxide layer 108, dye particles 110, and quantum dots 112. For example, the nanoporous titanium oxide layer 106 is coated on the plurality of twisted carbon nanotube yarns 102. FIG. 3 is a scanning electron microscope image of the nanoporous titanium oxide layer 106. The microporous titanium oxide layer 108 is then coated onto the nanoporous titanium oxide layer 106. FIG. 4 is a scanning electron microscope image the microporous titanium oxide layer 108.

Figure 5:
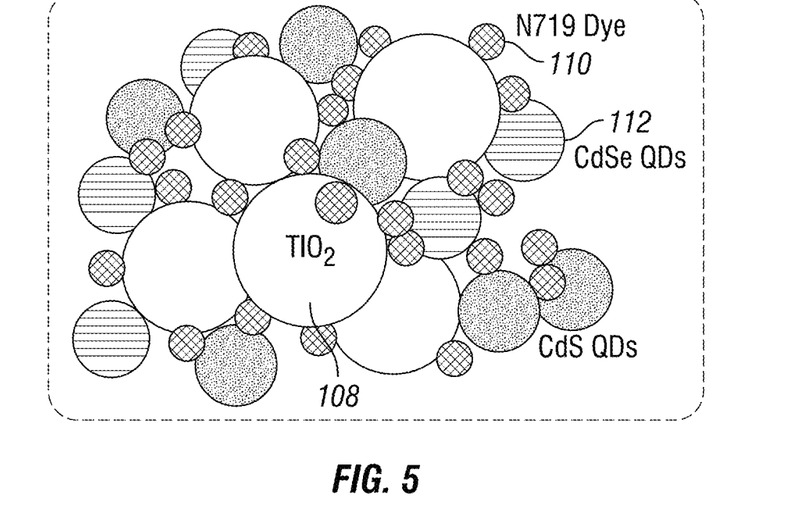
FIG. 5 schematically depicts an $np\text{-}TiO_2/mp\text{-}TiO_2/CdS/CdSe/N719$ hybrid photovoltaic sensitizer structure.
Figure 6:
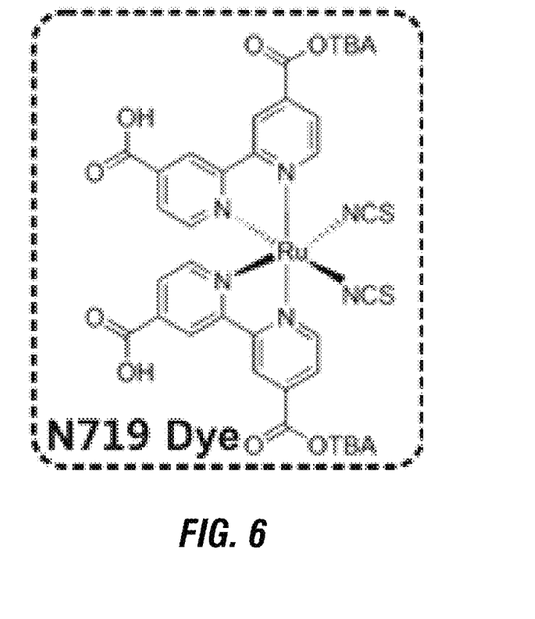
FIG. 6 depicts the chemical structure of an N719 dye.
Figure 8:
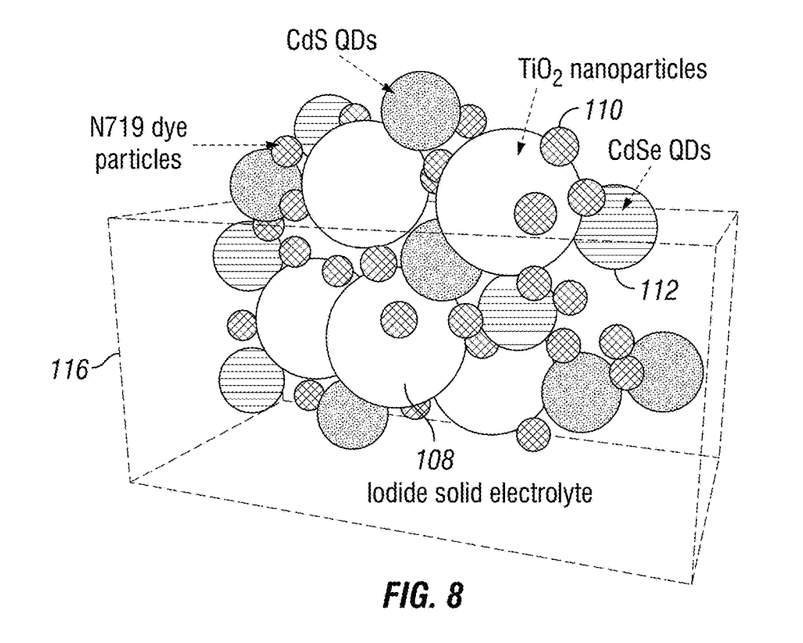
FIG. 8 schematically depicts a solid state electrolyte disposed about a hybrid photovoltaic sensitizer structure.

As depicted in FIGS. 1, 5, and 8, the dye particles 110 and the quantum dots 112 are disposed in the pores of the microporous titanium oxide layer 108. In some instances, the dye particles comprise N719 dye, which is depicted in FIG. 6. Any suitable dye particles may be used herein. In some instances, the quantum dots comprise CdS and CdSe. Any suitable quantum dots may be used herein.

The incorporation of the quantum dots and dye particles improves the photon absorption coefficient, tunable band gap, and MEG effects of the DSSC 100. In particular, the dye particles 110 and quantum dots 112 act as an extra electron receiver in the $TiO_2$ film 106/108. This is synthesized in a secondary process known as post-hydrothermal process. In this manner, the DSSC 100 includes an np-$TiO_2$/mp-$TiO_2$/CdS/CdSe/N719 hybrid photovoltaic sensitizer structure 104 to realize both MEG effects and multiple electron transmission paths.

Figure 7:
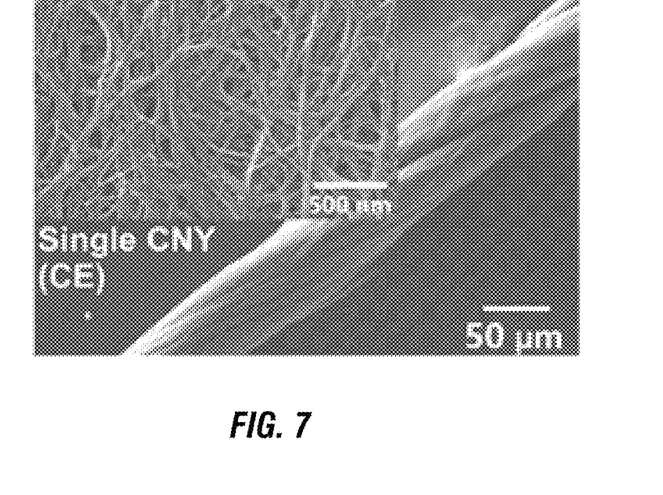
FIG. 7 depicts an SEM image of a conducting electrode comprises a single carbon nanotube yarn.

The DSSC 100 also includes a conducting electrode 114 disposed about the hybrid sensitizer 104. In some instances, the conducting electrode 114 comprises at least one carbon nanotube yarn. As depicted in in the scanning electron microscope image of FIG. 7, the conducting electrode 114 comprises a single carbon nanotube yarn. Any number of carbon nanotube yarns may be used herein. If more than one carbon nanotube yarn is used, the carbon nanotube yarns may be twisted or braided in any suitable configuration. As discussed below, the working electrode 102 and the conducting electrode 114 may be prepared in a similar manner.

As depicted in FIGS. 1 and 8, a solid state electrolyte 116 may be disposed about the hybrid sensitizer 104 and the conducting electrode 114. In some instances, the solid state electrolyte 116 comprises iodide solid electrolyte. Any suitable solid state electrolyte may be used herein. The solid iodide electrolyte improves the DSSC 100 performance and mechanical properties.

In one example embodiment, the carbon nanotube yarns of the working electrode and the conductive electrode were treated with 20 ml 70% (wt) $HNO_3$ (Sigma-Aldrich) for 3 min followed by rinsing with deionized water and acetone (Sigma-Aldrich) and thermal treatment for 2 h at 350° C. with argon flow (50 ml/min). The carbon nanotube yarns were rinsed with pure Triton-X 100 followed by deionized water and acetone (1 h) then dried at room temperature. The final step included rinsing pure Nano-water and drying in room temperature after washing the carbon nanotube yarns with 1.25 M $H_2SO_4$ and 0.55 M $(NH_4)_2S_2O_8$ for 1 h. The conducting electrode was platinized using sputtering target at 1.5 KV and 5 mA for 60 s. In this example, the working electrode included seven carbon nanotube yarns twisted together as a braid, while the conducting electrode comprised a single carbon nanotube yarn.

As noted above, the $TiO_2$ coating includes two parts: (1) np-$TiO_2$ coating; and (2) mp-$TiO_2$ coating. For these two layers, the np-$TiO_2$ thin film worked as a foundation layer for the nanostructured mp-$TiO_2$ layer, which provided a surface for a better attachment of the major coating (mp-$TiO_2$) and faster electron transportation for cells.

Np-$TiO_2$ coating solution is also known as Titanium isopropoxide (TIP) solution. TIP was used as a precursor of $TiO_2$. A solution was prepared as follows: TIP (0.02 M) was added to 2-isopropanol (50 ml) under vigorous stirring conditions and then triethyl amine (0.01 M) was added as a stabilizer of the solution and stirred (200 rpm) for 2-3 min under an inert environment. The inert environment was made by argon gas flow through the system. A second solution was then prepared separately as follows: hydrochloric acid (3.0 ml) and water (0.72 ml) were added to 2-isopropanol (50 ml) and mixed by a magnetic stirrer (200 rpm). These two solutions were then mixed together and stirred vigorously for 30 min under Ar gas flow. The formed TiO$_2$ sol was transparent, quite stable, and highly sensitive to the amount of triethylamine and water. For the impregnation, the working electrode, after being dried in a preheated oven as described before, was immersed for 30 s in the TiO$_2$ containing liquid solution. The extracted samples were then placed in 70° C. preheated oven to remove the solvent from the fiber and then heated at 95° C. for 5 min.

The preparation of the porous layer of TiO$_2$ was as follows: 30 mL pure Nano-water, 0.5 mL 70 wt % HNO$_3$ were mixed together as solution A. Solution B comprised 30 mL pure Nano-water, 2 mL Acetic Acid Glacia, 0.5 mL Triethylamine and 11.824 mL TiP. Solution A and B were prepared individually and mixed together after 5 min stirring. The mixture was heated in an autoclave at 240° C. for 12 h, and 50 vol % of the solvent of resultant solution were evaporated at 75° C. 5.2 g polyethylene glycol was added into the sol before coating. The working electrode was then immersed into these TiO$_2$ colloids via dip-coating method (5 s dipping followed by 5 min sintering in 350° C. air). This dip-coating-sintering process was repeated several times, where the number of repetitions determined the thickness of the TiO$_2$ thin film. In this example, this cycle was repeated 4 times to form a 20 µm thick porous coating layer.

The porous TiO$_2$ structure with quantum dots was prepared as follows: CdS and CdSe quantum dots were coated with a chemical bath deposition method. The working electrode was dipped into a 0.5 M Cd(NO$_3$)$_2$ ethanol solution for 5 min, rinsed with ethanol, and dried in the RT. This step was repeated twice before dipped for another 5 min into a 0.5 M Na$_2$S methanol solution and rinsed again with methanol. This whole cycle may be repeated twice for a mature coating. The preparation of CdSe quantum dots was similar except Na$_2$SeSO$_3$ solution was refluxed at 70° C. for 7 h, and a higher temperature (60° C.) and a longer time (1 h) were required during the dipping process.

With regard to the dye sensitizer, the treated electrodes were sensitized for 24 h by immersing into N719 (N719= [tetrabutylammonium] 2 [Ru (4-carboxylic acid-40-carboxy-late-2, 20-bipyridyl)2(NCS)2]) dye (0.05M N719 in the mixture of tert-Butanol and acetonitrile (volume ratio=1: 1)).

The solid electrolyte included 0.5 M LiI, 0.05 I$_2$ and 0.5 tert-butyl pyridine in 3-methoxy propionitrile (3-MePRN). Poly(vinylidene fluoride-co-hexafluoropropene) (5 wt %) was added to confirm the solid state of the electrolyte media.

In this example, cell performance was characterized by J-V curves which were measured with VersaSTAT3 (Electrochemical system with EIS capability, Princeton Applied Research, USA) at a potential scan rate of 50 mV/s cooperating with a solar simulator (Newport, Model 9129X, AM 1.5 illumination, light intensity 100 mW*cm$^{-2}$). To investigate the surface morphology and interface of electrodes, a field emission scanning electron microscope (SEM) (JOEL JSM-7410F) and a transmission/scanning transmission electron microscope (STEM/TEM) (JEM-ARM200cF) were used. Particularly, energy-dispersive X-ray spectroscopy (EDX) was also applied to finish elemental mapping and particle analysis/tracing.

Figure 9:
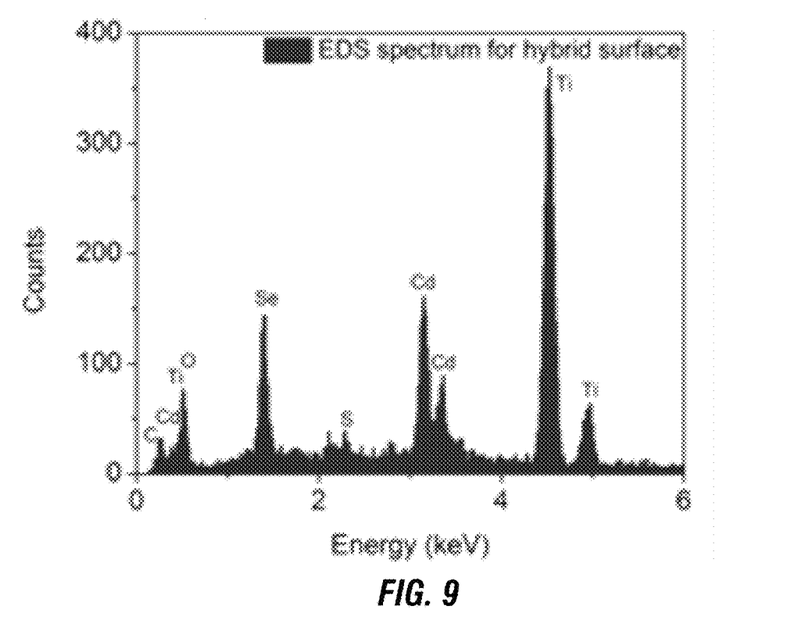
FIG. 9 depicts an energy dispersive spectroscopy spectrum for a hybrid photovoltaic sensitizer structure.

FIG. 9 depicts an energy dispersive spectroscopy (EDS) spectrum for the hybrid sensitizer. In this example, the hybrid sensitizer enhances photovoltaic cell performance. When light hits the dye particles on the cell surface, electrons are generated and transferred to either CdS or CdSe quantum dots. The electrons are then taken from quantum dots to the nanoporous TiO$_2$ phase, which has a larger band gap (3.2 eV). Simultaneously, the electrons will possibly be transferred from the dye particles to TiO$_2$ phase directly. These two methods are utilized together to accomplish the hybrid electron transmission pass. This way, more charges are generated, and a multiple excitation effect is achieved. Also, good dispersion of the quantum dots in the hybrid structure enhances the performance of cell and helps it to reach higher energy conversion efficiency.

Figure 10A:
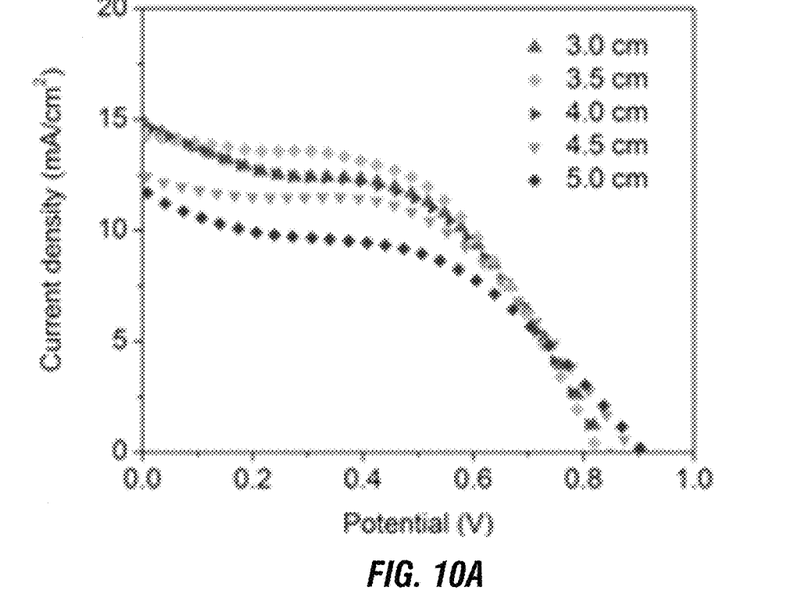
FIG. 10A depicts J-V curves of dye-sensitized solar cells using 1 carbon nanotube yarn as a conducting electrode with different cell lengths.
Figure 10B:
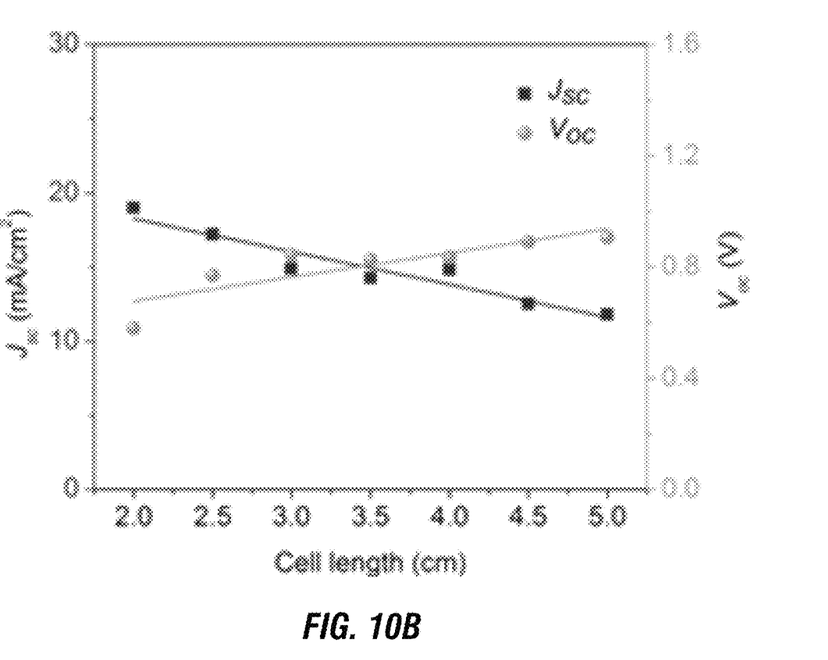
FIG. 10B depicts relative short-circuit current density and open-circuit voltage of dye-sensitized solar cells with different cell lengths.
Figure 10C:
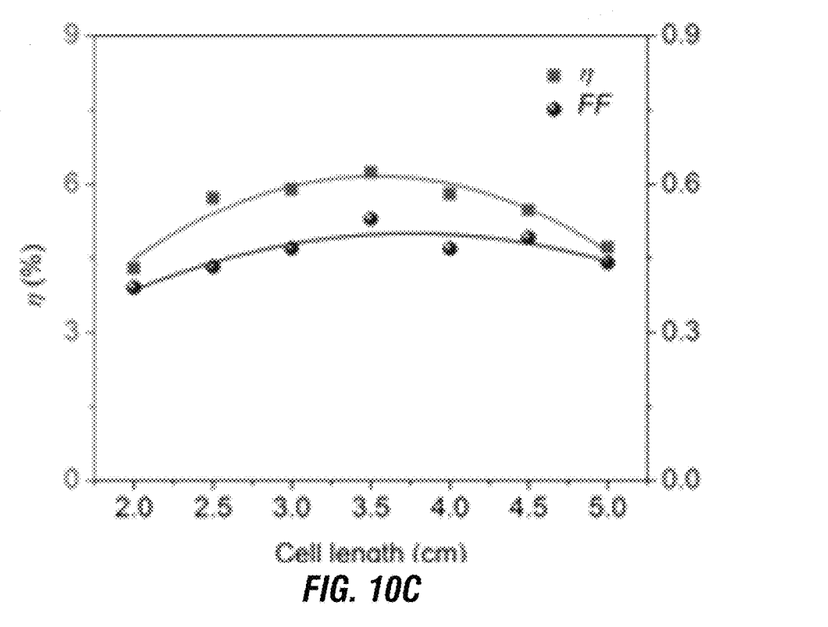
FIG. 10C depicts relative energy conversion efficiency and fill factor of dye-sensitized solar cells with different cell lengths.

FIGS. 10A-10C depict cell performance at various lengths. FIG. 10A depicts J-V curves of wire-shaped hybrid dye-sensitized solar cells using 1 carbon nanotube yarn as a conducting electrode with different cell lengths. As depicted in FIG. 10B, with the increase of cell length from 2.0 to 5.0 cm, J$_{SC}$ falls from 19.01 to 11.82 mA*cm$^{-2}$, while V$_{OC}$ is improved from 0.58 to 0.91 V. Overall, as depicted in FIG. 10C, energy conversion efficiencies and FFs can be maintained in a small dimension (Δη=1.52% and ΔFF=0.14), and 3.5 cm cell performs best in the comparison (η=6.24% and FF=0.53). Carbon nanotube yarns demonstrate certain resistance due to the complex overlaps of carbon nanotubes within, which is the cause of the parabolic performance variety.

Figure 10D:
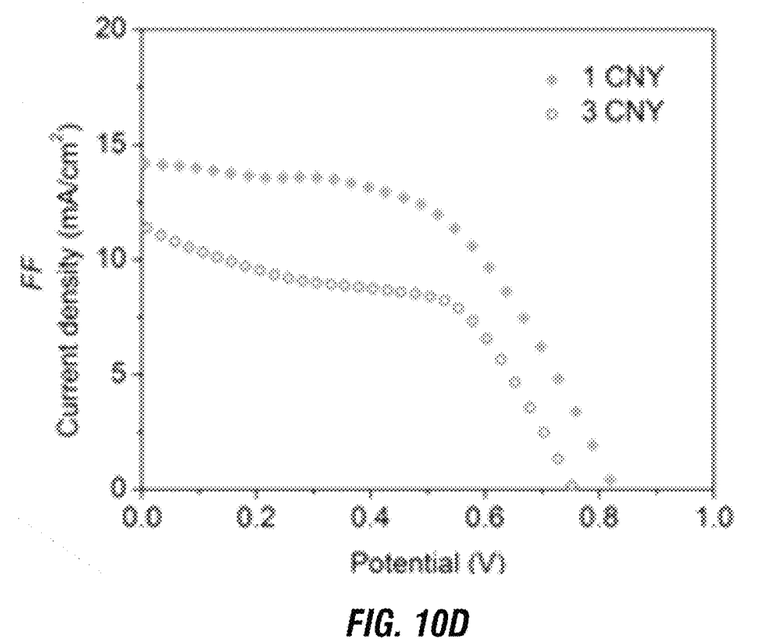
FIG. 10D depicts J-V curves of dye-sensitized solar cells using 1 carbon nanotube yarn and 3 carbon nanotube yarn as conducting electrodes.
Figure 10E:
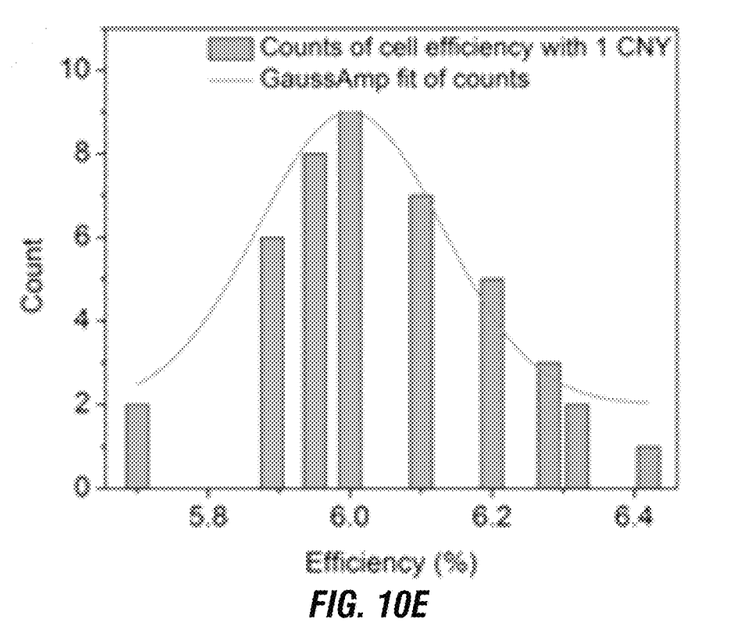
FIG. 10E depicts counts of dye-sensitized solar cell efficiency using 1 carbon nanotube yarn as conducting electrodes and the corresponding GaussAmp fit curve.
Figure 10F:
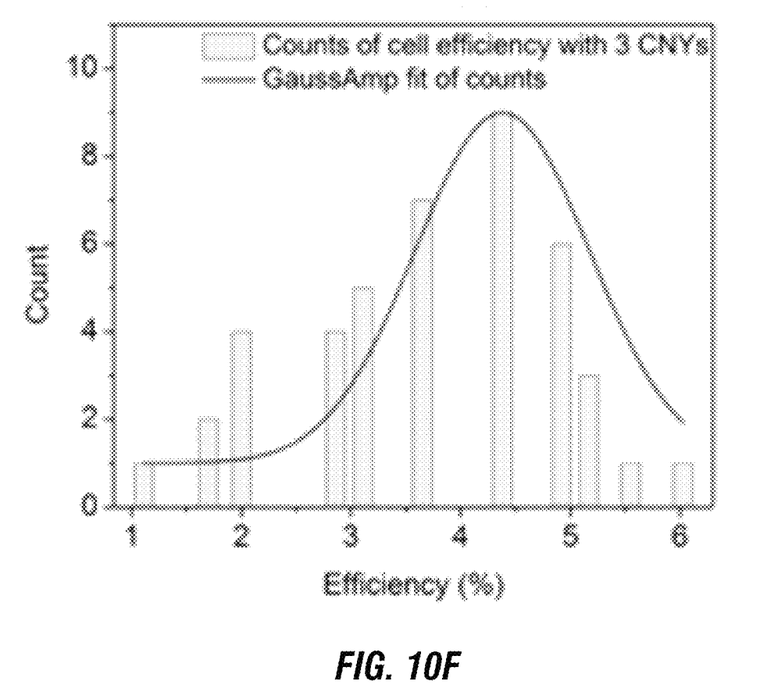
FIG. 10F depicts counts of dye-sensitized solar cell efficiency using 3 carbon nanotube yarns as conducting electrodes and the corresponding GaussAmp fit curve.

As shown in FIG. 10D, the influence of carbon conducting electrodes with different dimensions on performance of cells was demonstrated using conducting electrodes with 1 carbon nanotube yarn and 3 twisted carbon nanotube yarns. By replacing the 1 carbon nanotube yarn conducting electrode with 3 carbon nanotube yarns, the J$_{SC}$ falls from 14.268 to 11.473 mA*cm$^{-2}$, and the V$_{OC}$ decreased to 0.756 to 0.826 V. Correspondingly, the energy conversion efficiency has a 29.4% decrease (from 6.2% to 4.38%). Statistical results of the reproducibility are shown in FIGS. 10E and 10F. In general, cells with 1 carbon nanotube yarn conducting electrode have better cell performance than those with 3 twisted carbon nanotube yarns. 62% of those cells show energy conversion efficiencies of >6%. However, for the cells with 3 twisted carbon nanotube yarns, only 2.3% of them can achieve the energy conversion efficiency more than 6%. This significant difference may also be observed from the curve peaks (6.0% for 1 carbon nanotube yarn and 4.38% for 3 carbon nanotube yarns). In this manner, smaller dimension conducting electrodes may help cell to achieve better performance (up to 6.4%). This may be as a result of the simpler structure yielding higher photoelectron conductivity.

Figure 11A:
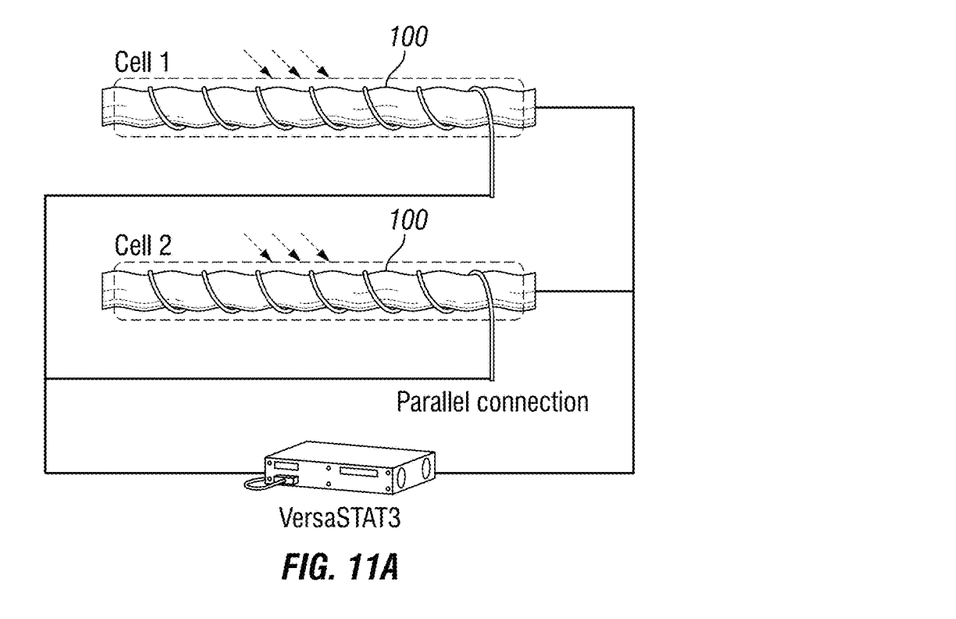
FIG. 11A schematically depicts two dye-sensitized solar cells in parallel connection.
Figure 11B:
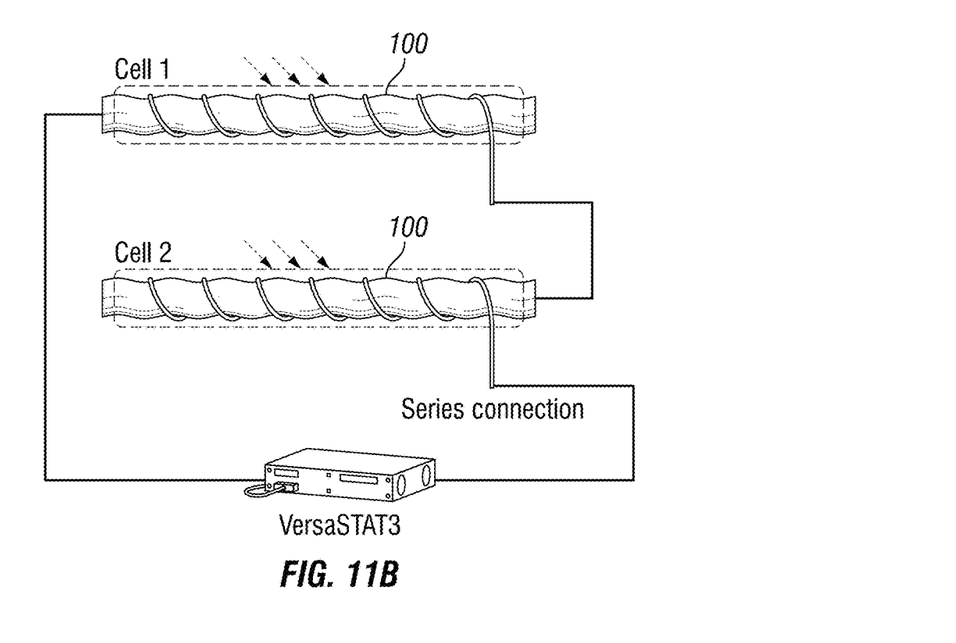
FIG. 11B schematically depicts two dye-sensitized solar cells in series connection.
Figure 11C:
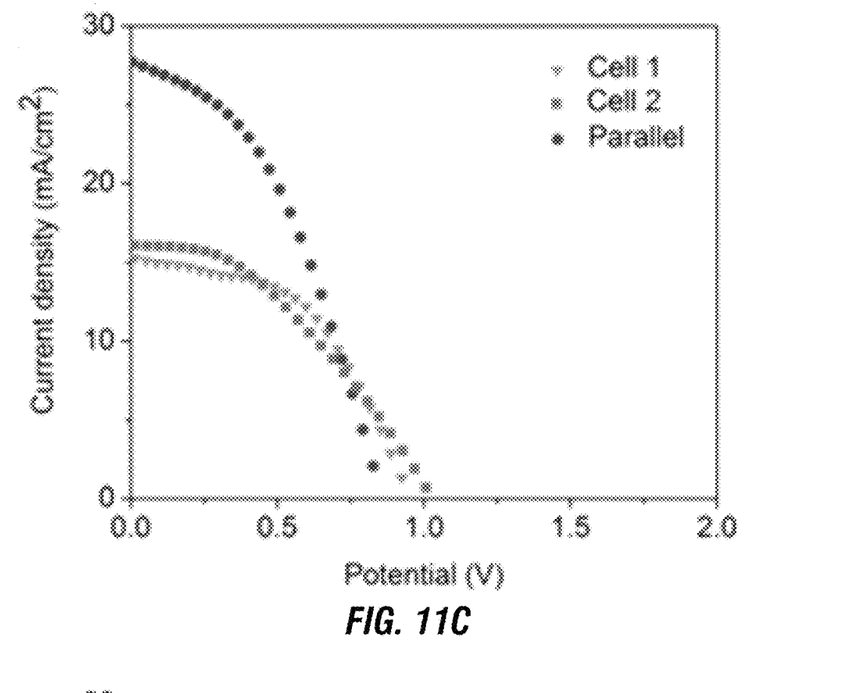
FIG. 11C depicts J-V curves of two comparable dye-sensitized solar cells and cells under parallel connection.
Figure 11D:
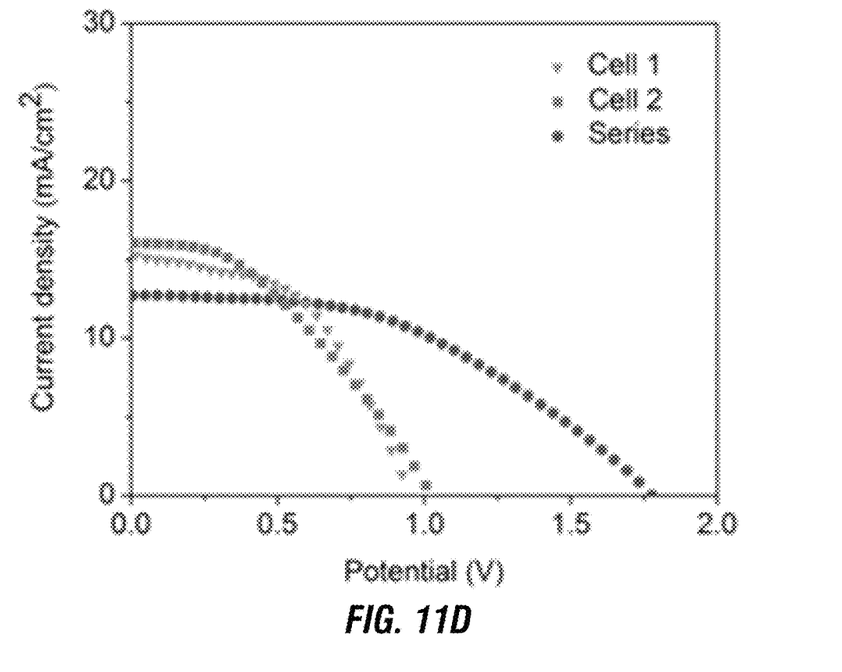
FIG. 11D depicts J-V curves of two comparable dye-sensitized solar cells and cells under series connection.

FIGS. 11A-12E depict one or more engineering applications of the DSSC 100. FIG. 11A depicts two DSSC 100 in parallel connection, and FIG. 11B depicts two DSSC 100 in series connection. The connections between two DSSCs 100 can cause unavoidable resistance in the circuit. For example, as depicted in FIGS. 11C and 11D, the I$_{SC}$ of two parallel cells (1.39 mA) is approximately the sum of two individual ones, while the value of V$_{OC}$ of two series cells (1.77 V) is slightly less than the sum of them. It can be concluded that cells under series/parallel connections can still maintain stable and keep working in an allowable deviation. These results support the quest to apply these wire-shaped flexible 3D DSSCs into required engineering applications, such as through a weaving process in fabricating with engineering textiles.

Figure 12A:
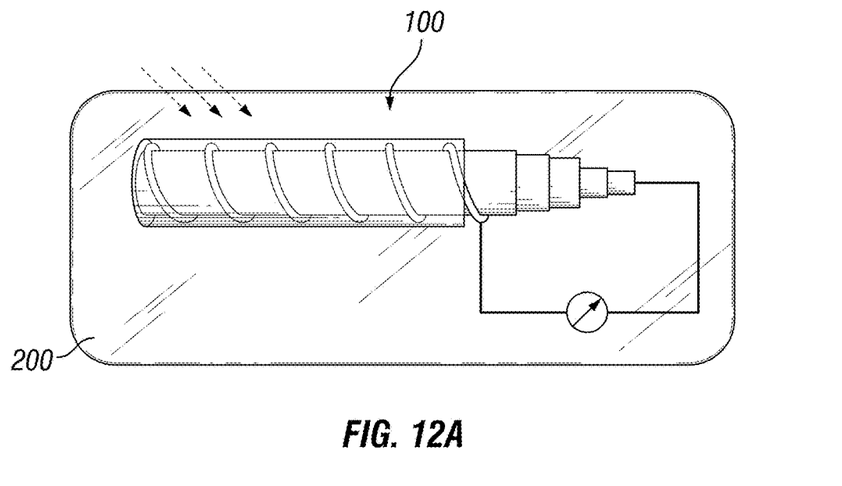
FIG. 12A schematically depicts a perspective view of a dye-sensitized solar cell tested with a mirror beneath.
Figure 12B:
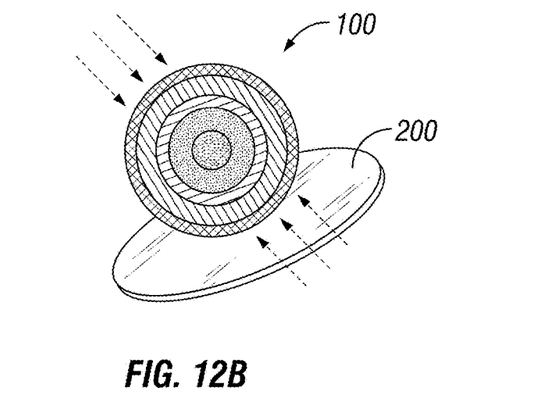
FIG. 12B schematically depicts a cross-sectional view of a dye-sensitized solar cell tested with a mirror beneath.
Figure 12C:
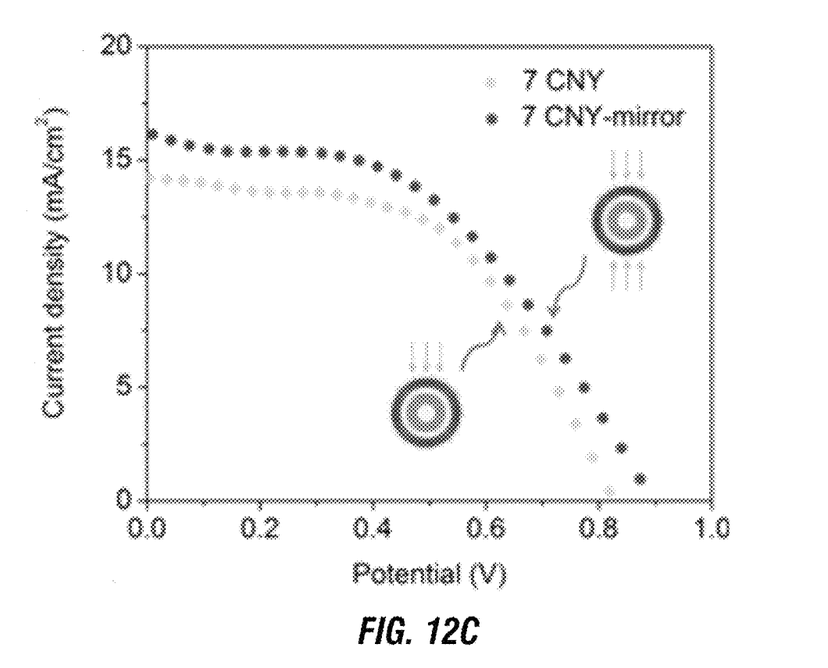
FIG. 12C depicts J-V curves of a dye-sensitized solar cell with and without a mirror beneath.
Figure 12D:
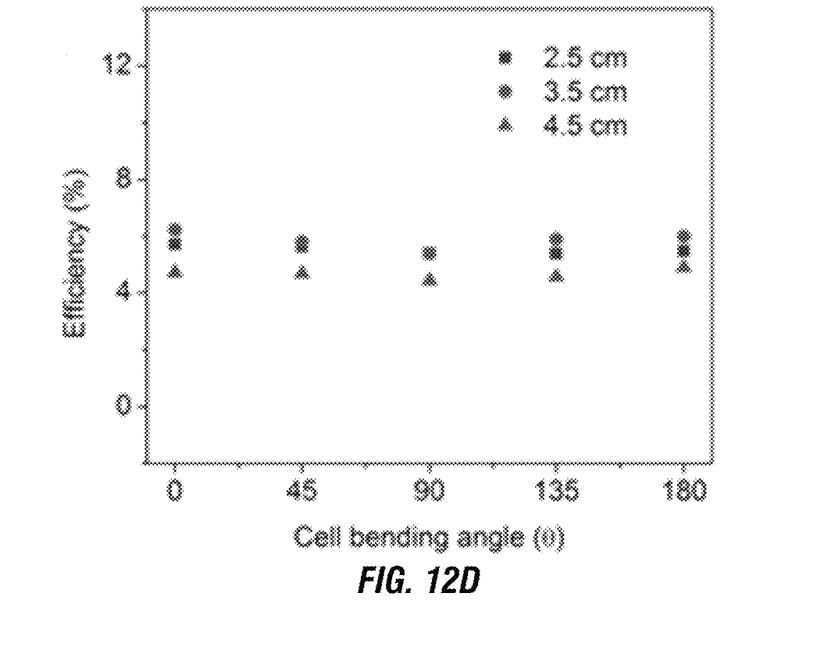
FIG. 12D depicts energy conversion efficiency of dye-sensitized solar cells with different bending angles and cell lengths.
Figure 12E:
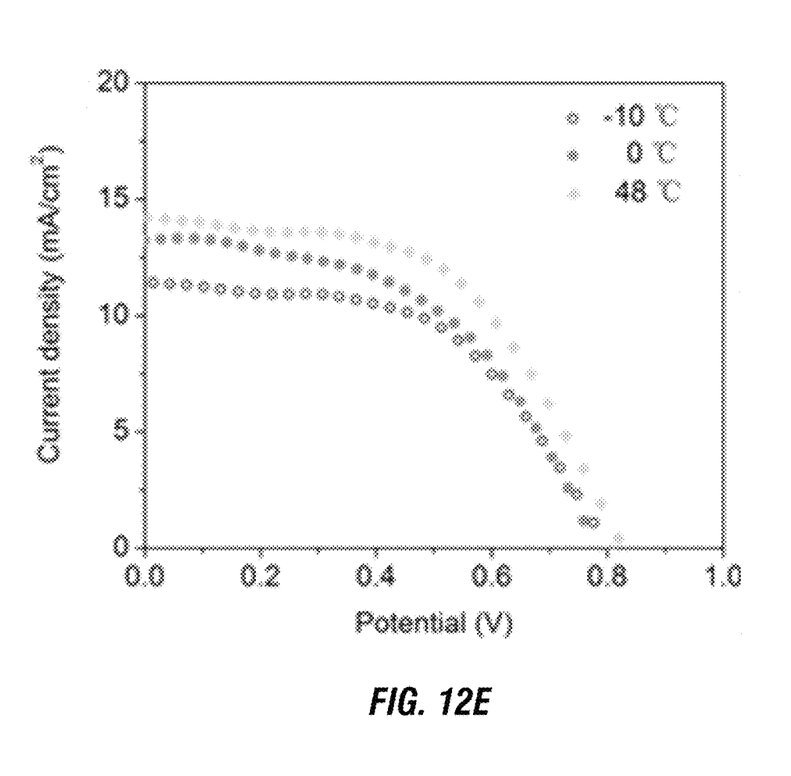
FIG. 12E depicts J-V curves of a dye-sensitized solar cell at different temperatures.

DSSCs have been recognized for their energy conversion capacity. However, practical engineering applications outside solar panels have not been truly developed. In FIGS. 12A-12E, various light intensity, cell bending angles, and working temperatures have been tested to determine if the DSSC 100 can maintain stable, which it can. For example, as depicted in FIGS. 12A and 12B, the DSSC 100 was located adjacent to a mirror 200. As depicted in FIG. 12C, the addition of the mirror 200 underneath the DSSC 100 increased stability by 7.39%. This great stability and cell flexibility ensures the possibility of incorporating cells into practical structures. FIG. 12D depicts energy conversion efficiency of wire-shaped hybrid dye-sensitized solar cells with different bending angles and cell lengths, and FIG. 12E depicts J-V curves of a wire-shaped hybrid dye-sensitized solar cell at different temperatures.

Although specific embodiments of the disclosure have been described, numerous other modifications and alternative embodiments are within the scope of the disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

We claim:

1. A dye-sensitized solar cell, comprising:
   a working electrode comprising seven twisted carbon nanotube yarns;
   a hybrid sensitizer which comprises:
      a nanoporous titanium oxide layer coated on the seven twisted carbon nanotube yarns,
      a microporous titanium oxide layer coated onto the nanoporous titanium oxide layer, and
      dye particles and quantum dots disposed in the pores of the microporous titanium oxide layer, wherein the dye particles comprise N719 dye, and the quantum dots comprise CdS and CdSe;
   a conducting electrode comprising one carbon nanotube yarn disposed about the hybrid sensitizer or three twisted carbon nanotube yarns disposed about the hybrid sensitizer; and
   a solid state electrolyte disposed about the hybrid sensitizer.

2. The dye-sensitized solar cell of claim 1, wherein the solid state electrolyte comprises iodide solid electrolyte.

3. The dye-sensitized solar cell of claim 1, wherein the seven twisted carbon nanotube yarns form a braided structure.

4. The dye-sensitized solar cell of claim 1, wherein the dye-sensitized solar cell is in the form of flexible wire.

5. A woven fabric which comprises two or more of the dye-sensitized solar cells of claim 1.

6. A method comprising:
   providing the dye-sensitized solar cell of claim 1 incorporated into a structure; and
   using the dye-sensitized solar cell to detect a status of the structure,
   wherein using the dye-sensitized solar cell comprises triboluminescent-based monitoring of the health of the structure.

7. A method comprising:
   providing a photovoltaic cell which comprises the dye-sensitized solar cell of claim 1; and
   using the dye-sensitized solar cell to harvest energy.

8. A flexible, wire-shaped dye-sensitized solar cell, comprising:
   a working electrode comprising seven twisted carbon nanotube yarns;
   a hybrid sensitizer, comprising:
      a porous metal oxide layer coated on the seven twisted carbon nanotube yarns, and
      dye particles and quantum dots located in or on the porous metal oxide layer, wherein the dye particles comprise N719 dye, and the quantum dots comprise CdS and CdSe;
   a conducting electrode comprising one carbon nanotube yarn disposed about the hybrid sensitizer or three twisted carbon nanotube yarns disposed about the hybrid sensitizer; and
   a solid state electrolyte disposed about the hybrid sensitizer.

9. The dye-sensitized solar cell of claim 8, wherein the seven twisted carbon nanotube yarns are in a braided structure form.

10. The flexible, wire-shaped dye-sensitized solar cell of claim 8, wherein the solid state electrolyte comprises iodide solid electrolyte.

11. A woven fabric which comprises two or more of the flexible, wire-shaped dye-sensitized solar cells of claim 8.

12. A method of manufacturing a dye-sensitized solar cell, comprising:
   twisting seven carbon nanotube yarns to form a working electrode;
   coating a layer of nanoporous titanium oxide on the seven twisted carbon nanotube yarns;
   coating a layer of microporous titanium oxide onto the nanoporous titanium oxide layer;
   positioning dye particles and quantum dots in the pores of the microporous titanium oxide layer,
   wherein the quantum dots comprise CdS and CdSe and the dye particles comprise N719 dye;
   wherein the layer of nanoporous titanium oxide, the layer of microporous titanium oxide, the dye particles, and the quantum dots collectively form a hybrid sensitizer;
   providing a conducting electrode comprising one carbon nanotube yarn disposed about the hybrid sensitizer or three twisted carbon nanotube yarns disposed about the hybrid sensitizer; and
   providing a solid state electrolyte about the hybrid sensitizer.

13. The method of claim 12, wherein the solid state electrolyte comprises iodide solid electrolyte.

* * * * *